United States Patent [19]

Kitamura et al.

[11] Patent Number: 4,772,660

[45] Date of Patent: Sep. 20, 1988

[54] OXIDE SOL USING REACTIVE MONOMER AS DISPERSION MEDIUM

[75] Inventors: Shuji Kitamura, Nagaokakyo; Kiyohiko Nakae, Nishinomiya; Haruo Hayashida, Osaka; Seiichi Shibata, Takatsuki, all of Japan

[73] Assignee: Sumitomo Chemical Company, Limited, Osaka, Japan

[21] Appl. No.: 917,560

[22] Filed: Oct. 10, 1986

[30] Foreign Application Priority Data

Oct. 18, 1985 [JP] Japan .................. 60-234129

[51] Int. Cl.$^4$ ............................................. C08K 3/10
[52] U.S. Cl. ....................... 524/786; 524/789; 524/847; 524/430; 524/492; 524/493
[58] Field of Search ............ 524/786, 847, 430, 492, 524/493, 789

[56] References Cited

U.S. PATENT DOCUMENTS 3,960,805  6/1976  Taylor ................................ 524/786
4,104,243  8/1978  Howard .............................. 524/786

FOREIGN PATENT DOCUMENTS 14698  2/1967  Japan .
8614   1/1984  Japan .

OTHER PUBLICATIONS

Hackh's Chemical Dictionary, fourth edition, 1972, p. 622.

*Primary Examiner*—Joseph L. Schofer
*Assistant Examiner*—Peter D. Mulcahy
*Attorney, Agent, or Firm*—Stevens, Davis, Miller & Mosher

[57] ABSTRACT

The present invention provides an oxide sol hardened by the irradiation of actinic rays such as UV ray, electron ray, $\gamma$ ray, X ray etc., by heating or by using a catalyst. Said oxide sol comprises not less than 20% by weight of an oxide such as $SiO_2$, $Al_2O_3$ or the like in a dispersion medium containing at least 80% by mole of a reactive monomer such as acrylic acid, its esters, $\alpha$-substituted acrylic acid esters, etc.

These oxide sols have a good coating property and stable compatibility with organic solvents and are useful as modifiers for resins, binders for ceramics, thickening agents for cosmetics, coating agents for paper, antistatic agents for fabrics.

4 Claims, No Drawings

OXIDE SOL USING REACTIVE MONOMER AS DISPERSION MEDIUM

TECHNICAL FIELD OF THE INVENTION

This invention relates to an oxide sol which undergoes hardening by the irradiation of actinic energy rays such as ultraviolet ray, electron ray, $\gamma$ ray, X ray and the like by heating, or by the use of a catalyst.

The term "hardening" means herein a phenomenon involving polymerization or cross-linking.

Oxide sols are used in a variety of fields including modifiers for resins, binders for ceramics, thickening agents for cosmetics, coating agents for paper and antistatic agents for fibers by virtue of their strong points including good coating property and stable compatibility with organic solvents.

OBJECTS OF THE INVENTION

An object of this invention is to suppress the contractions due to the polymerization of reactive monomers with the aid of oxide particles. Another object is to make such properties as infrared absorptivity which are inherent to the oxide be exhibited in the product obtained after hardening by polymerization.

Thus, this invention relates to an oxide sol in which at least 80% by mole of its dispersion medium is comprised with a reactive monomer which has in its molecule the polymerizable unsaturated bond(s) which undergoes hardening by the irradiation of actinic energy rays such as ultraviolet ray, electron ray, $\gamma$ ray, X ray and the like or by heating. This invention makes it possible to suppress the contractions due to the polymerization of the reactive monomer and to make such properties as infrared absorptivity which are inherent to the oxide be exhibited in hardened products. Accordingly, this invention can be applied not only to the above-mentioned uses but also, as a surface modification means, to agricultural covering materials.

PRIOR ART

Since a reactive monomer generally has a lower density a compared with that of the polymer produced by its polymerization, the polymerization is accompanied with volume contraction. For example, when such a monomer was coated on a film substrate and was hardened by means of actinic energy rays or heating, wrinkles were observed to form.

Further, since the prior art oxide sol uses water or organic solvents such as methanol as a dispersion medium, the presence of such a dispersion medium caused serious problems when the sol was added to a reactive monomer in an attempt to suppress the contractions in hardening.

Thus, when a reactive monomer is mixed with a hydrosol or an organosol using methanol etc. as a dispersion medium and is hardened by the irradiation of actinic rays or heating, it is necessary for the dispersion medium to be evaporated off and consequently there occur the problems of needing an evaporation step and possible environmental pollution and further, when the hardening is effected by actinic rays, the problem of failure of continuous irradiation due to the condensation of evaporated product taking place in an irradiation chamber or a duct, and when the hardening is effected by heating, the problem of needing explosion-proof equipment. Accordingly, such methods were not useful in practice.

CONSTRUCTION OF THE INVENTION

After extensive studies, however, the present inventors have invented an oxide sol which uses as a dispersion medium a reactive monomer having polymerizable unsaturated bonds in the molecule.

Thus, the use of a reactive monomer itself as a dispersion medium has made it possible to suppress the contraction in polymerization with the aid of oxide particles and further to make such properties as infrared absorptivity which are inherent to the oxide be exhibited in the hardened product. However, the reactive monomer should account for at least 80% by mole of the dispersion medium because when the proportion of the reactive monomer in the dispersion medium is less than 80% by mole there occur such problems as the condensation of the remaining unpolymerizable dispersion medium which results from its vaporization as mentioned above. As examples of oxide sols, mention may be made here of silica sol, alumina sol and iron sol.

The reactive monomer which has polymerizable unsaturated bond(s) in the molecule referred to herein may be any organic compound which contains double or triple bond between carbon atoms and undergoes hardening by heating or by the use of catalysts as well as by actinic energy rays.

Further, the reactive monomer can be used not only in the form of a monomer but also as an oligomer or a prepolymer so long as they are liquid at ordinary temperatures. These may be used each alone or as a mixture thereof.

Reactive monomers which have, among polymerizable unsaturated bonds, particularly ethylenic unsaturated bond(s) can be used in this invention because of their excellent properties including ease of handling.

Reactive monomers which have an ethylenic unsaturated bond referred to herein mean monomers having ethylenic linkage(s). These may be hydrocarbon compounds or may be those having a variety of functional groups. As examples of such monomers, mention may be made of olefins such as ethylene, propylene and butylene; dienes such as butadiene, 1,4-pentadiene, and 1,5-hexadiene; olefinic aromatic hydrocarbons such as styrene, vinyltoluene, and $\alpha$-methylstyrene; halogenated olefins such as vinyl chloride and vinylidene chloride; fatty acid alkenyl esters such as vinyl acetate, vinyl propionate, vinyl butyrate, and isopropenyl acetate; unsaturated carboxylic acids such as acrylic acid and methacrylic acid; acrylic esters such as methyl acrylate, ethyl acrylate, propyl acrylate, and octyl acrylate; methacrylic esters such as methyl methacrylate, butyl methacrylate, and 2-ethylhexyl methacrylate; and acrylic acid derivatives such as acrylamide and acrylonitrile.

The present inventors have made a further study on reactive monomers having ethylenic unsaturated bond(s), and resultantly found that those which have in the molecule an atomic group represented by the following general formula

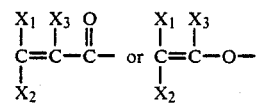

wherein $X_1$, $X_2$ and $X_3$ denote any one of a hydrogen atom, an alkyl group and a carboxyl group, are favorable reactive monomers in this invention because of their high reactivity. When atomic groups bonded to the above-mentioned atomic groups are denoted by Y and Z, namely

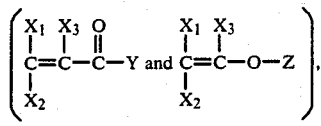

examples of Y include, for example, —R, —OR, and —NR and those of Z include —R and

wherein R indicates hydrogen or an alkyl group.

As specific examples, there may be mentioned ethylenically unsaturated carboxylic acids such as acrylic acid, methacrylic acid, maleic acid, fumaric acid, crotonic acid, and itaconic acid; ethylenically unsaturated carboxylic anhydrides such as maleic anhydride and tetrahydrophthalic anhydride; ethylenically unsaturated esters and fatty acid alkenyl esters such as ethyl acrylate, methyl methacrylate, 2-ethylhexyl acrylate, and vinyl acetate; ethylenically unsaturated amides or imides such as acrylamide, methacrylamide, and maleimide; and ethylenically unsaturated aldehydes or ketones such as acrolein, methacrolein, vinyl methyl ketone, and vinyl butyl ketone.

Further, particularly preferable among these are acrylic acid, acrylic esters, or α-substituted acrylic acid esters. As examples of acrylic esters or α-substituted acrylic acid esters, there may be listed the following.

Acrylic acid alkyl and cycloalkyl esters such as methyl acrylate, ethyl acrylate, n-propyl acrylate, isobutyl acrylate, n-amyl acrylate, n-hexyl acrylate, cyclohexyl acrylate, and n-octyl acrylate; acrylic acid halogenated alkyl esters such as 2-chloroethyl acrylate and 3-chloropropyl acrylate; acrylic acid hydroxyalkyl esters having a hydroxyl group such as 2-hydroxyethyl acrylate and 2-hydroxypropyl acrylate; acrylic esters having an ether ring such as glycidyl acrylate and tetrahydrofurfuryl acrylate; acrylic esters containing an aromatic ring such as benzyl acrylate; α-alkylacrylic acid alkyl and cycloalkyl esters such as methyl methacrylate, ethyl methacrylate, n-propyl methacrylate, isopropyl methacrylate, n-butyl methacrylate, isobutyl methacrylate, cyclohexyl methacrylate, n-octyl methacrylate, and lauryl methacrylate; α-halogenoacrylic esters such as methyl α-chloroacrylate and ethyl α-chloroacrylate; α-alkylacrylic acid halogenated alkyl esters such as 2-chloroethyl methacrylate and 3-chloropropyl methacrylate; α-alkylacrylic acid esters having a hydroxyl group such as 2-hydroxyethyl methacrylate and 2-hydroxypropyl methacrylate; and methacrylic esters containing an ether ring such as glycidyl methacrylate and tetrahydrofurfuryl methacrylate are included.

The concentration of the solid in the oxide sol is favorably not less than 20% by weight and not more than 70% by weight. When the concentration of the solid in the oxide sol is less than 20% by weight, contraction in polymerization is not always satisfactorily suppressed even when such properties as infrared absorptivity inherent to the oxide are exhibited with sufficient effectiveness; whereas when the solid concentration exceeds 70% by weight the sol tends to undergo gelation. Thus, the concentration of the solid in the oxide sol is preferably not less than 20% by weight and not more than 70% by weight.

An oxide sol of this invention can be prepared, for example, by a method which comprises blowing a reactive monomer into a hydrosol of or an organosol using an unpolymerizable organic solvent as a dispersing medium, of the oxide and then distilling the water or organic solvent off under reduced pressure, thereby replacing the dispersion medium with the reactive monomer.

This invention will be concretely illustrated below with reference to Examples, but it is in no way limited thereto.

EXAMPLE 1

Into a silica sol (solid concentration: 30% by weight) using methanol as a dispersion medium, was blown 2-hydroxyethyl acrylate, and methanol was gradually distilled out at a reduced pressure of 50 mmHg. Thus, 99.5% by mole of the dispersing medium was replaced with 2-hydroxyethyl acrylate over a period of about 6 hours. The solid concentration of $SiO_2$ at that time was 28% by weight and the viscosity was 18 c.p. as determined with a Brookfield type viscometer.

The silica sol using 2-hydroxyacrylate as a dispersion medium thus obtained was coated in a wet thickness of 10 μm on a LDPE (Sumikathene ® F101-1) film of 100 μm thickness. It was then subjected to continuous irradiation under conditions of an acceleration voltage of 200 Kev and an absorbed dose of 10 Mrad by use of an area-beam type electron ray irradiation apparatus (Curetron ®, mfd. by Nisshin High-voltage K.K.). The travelling speed of the film was 12 m/min. On observation of the irradiation duct after 10 minutes of irradiation, no condensation product was recognized in the duct. Further, the obtained film developed no wrinkles and had a good appearance. The results are shown in Table 1.

EXAMPLES 2 to 5, COMPARATIVE EXAMPLE 1

Other sols were also investigated in the same manner as in Example 1.

The results obtained are shown in Table 1.

COMPARATIVE EXAMPLE 2

A silica sol (solid concentration: 30% by weight) using water as a dispersion medium was coated in a wet thickness of 10 μm on the LDPE film of Example 1, and passed through an oven at 80° C. at a film travelling speed of 2 m/min (residence time in the oven: 5 minutes) to form a $SiO_2$ coating on the film surface, which coating however, soon peeled off the film. Thus no satisfactory product was obtained.

TABLE 1

| Starting Sol | | | Oxide sols and their properties | | | | Election ray irradiation | | |
| --- | --- | --- | --- | --- | --- | --- | --- | --- | --- |
| | | | Oxide sol obtained | | | | | | |
| Dispersion medium | Oxide | Solid concentration (% by wt.) | Dispersion medium | Replaced amount (% by mole) | Solid concentration (% by wt.) | Viscosity (c.p.) | Presence of condensation in duct | Film appearance (presence of wrinkles) | Remarks |
| Methanol | $SiO_2$ | 30 | 2-Hydroxyethyl acrylate | 99.5 | 28 | 18 | | | Example 1 |
| " | " | " | 2-Hydroxyethyl acrylate | 98 | 55 | 80 | | | Example 2 |
| " | " | " | 2-Hydroxyethyl methacrylate | 95 | 50 | 65 | | | Example 3 |
| Water | " | 40 | Acrylic acid | 82 | 43 | 38 | | | Example 4 |
| " | $Al_2O_3$ | " | Acrylic acid | 90 | 35 | 25 | | | Example 5 |
| Methanol | $SiO_2$ | 30 | Methyl acrylate | 50 | 25 | 8 | X | | Comparative Example 1 |

What is claimed is:

1. A silica or alumina sol comprising 20% to 70% by weight of silica or alumina dispersed in a medium comprising 80 to 100 mole % of a reactive monomer having a polymerizable unsaturated bond and 20 to 0 mole % of water or methanol.

2. The silica or alumina sol accoridng to claim 1, wherein the polymerizable unsaturated bond is an ethylenic unsaturated bond.

3. The silica or alumina sol according to claim 1, wherein the reactive monomer having polymerizable unsaturated bond is one which has in its molecule an atomic group represented by the following general formula

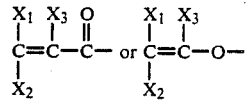

where $X_1$, $X_2$ and $X_3$ represent any one of hydrogen atom, alkyl group and carboxyl group.

4. The silica or alumina sol according to claim 1, wherein the reactive monomer having a polymerizable unsaturated bond is acrylic acid, an acrylic ester, or an alpha-substituted acrylic ester.

* * * * *